United States Patent [19]

Crum

[11] Patent Number: 4,514,261

[45] Date of Patent: Apr. 30, 1985

[54] REFINING OF TERTIARY BUTYLSTYRENE

[75] Inventor: Glen F. Crum, Odessa, Tex.

[73] Assignee: El Paso Products Company, Odessa, Tex.

[21] Appl. No.: 646,267

[22] Filed: Aug. 31, 1984

[51] Int. Cl.³ .............................. B01D 3/40; C07C 7/08
[52] U.S. Cl. ............................................ 203/9; 203/58; 203/91; 585/806; 585/807; 585/857
[58] Field of Search .................. 203/58, 69, 9, 68, 65, 203/91; 208/325, 321; 585/445, 443, 444, 5, 804, 805, 809, 811, 807, 806, 857

[56] References Cited

U.S. PATENT DOCUMENTS

| | | | |
|---|---|---|---|
| 3,466,344 | 9/1969 | Graff et al. | 203/58 |
| 3,605,850 | 9/1971 | Borst, Jr. | 208/325 |
| 3,706,811 | 12/1972 | Duke, Jr. | 585/445 |
| 4,033,829 | 7/1977 | Higgins, Jr. et al. | 203/9 |
| 4,040,911 | 8/1977 | Bacha et al. | 203/9 |
| 4,086,147 | 4/1978 | Watson | 203/9 |
| 4,182,658 | 7/1980 | Watson | 203/69 |
| 4,272,344 | 6/1981 | Watson | 203/65 |
| 4,291,183 | 9/1981 | Crum et al. | 585/444 |
| 4,376,678 | 3/1983 | Partos | 203/65 |
| 4,457,806 | 7/1984 | Grivas et al. | 203/65 |

OTHER PUBLICATIONS

*Hydrocarbon Processing*, "A Better Way to Extract Aromatics", vol. 38, No. 9, Sep. 1959, pp. 185–192.

Primary Examiner—Wilbur Bascomb
Assistant Examiner—V. Manoharan
Attorney, Agent, or Firm—Fred S. Valles; Margareta LeMaire

[57] ABSTRACT

Isopropenylstyrene, present in t-butylstyrene in small quantities as an impurity, is removed by extractive distillation using sulfolane as solvent.

10 Claims, 1 Drawing Figure

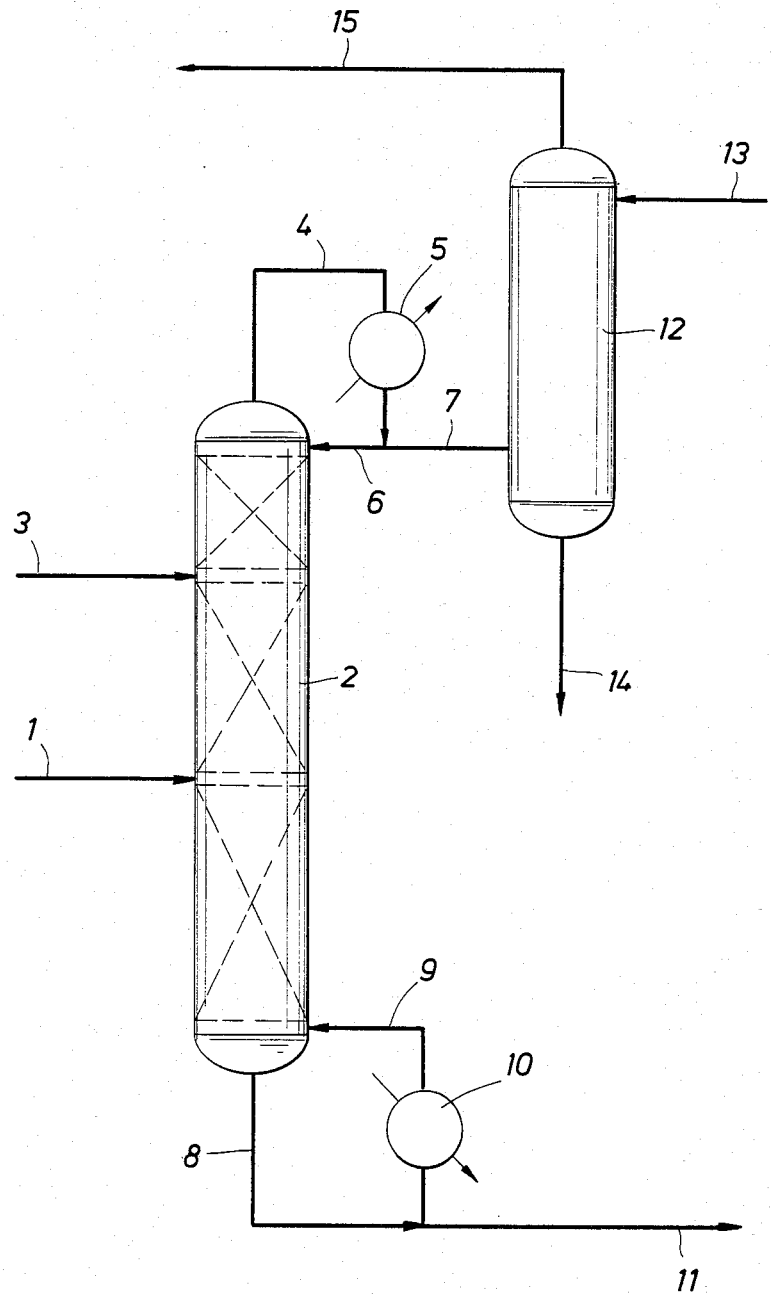

REFINING OF TERTIARY BUTYLSTYRENE

BACKGROUND OF THE INVENTION

The invention relates broadly to the manufacture of pure t-butylstyrene and in particular to the refining of t-butylstyrene for removal of isopropenylstyrene impurities.

Tertiary-butylstyrene (tBS) is a compound which is advantageously prepared by catalytic oxydehydrogenation of t-butylethylbenzene (tBEB). It has many uses, e.g. as a chemical intermediate, as a monomer or comonomer in the production of polymeric materials and the like. Tertiary-butylstyrene has often replaced styrene in some applications because desirable physical and chemical product properties result from such a substitution. In addition, there are processes where styrene is not suitable but where tertiary-butylstyrene functions well.

Because tBS belongs to the same family as styrene, there are similarities in the chemistry. One of the common properties is the tendency for the styrenics to polymerize whenever they are activated by chemicals or by heat. Some of the techniques used in purifying styrene can be used to purify tBS. However, because the boiling point of tBS is about 70° C. higher than that of styrene, the tendency for tBS to polymerize is much greater than that of styrene in any of the commercial processes for purifying styrene.

Some of the differences between styrene and tBS are derived from the compounds of the dialkenylbenzene family, that are present in tBS but not in styrene. These crosslinking compounds can polymerize to give a type of polymer that interferes with the operation of refining equipment. The crosslinked polymer has a tendency to collect in the equipment and to resist attempts to dissolve it.

In addition to some higher boiling hydrocarbon contaminants, there are particularly two dialkenylbenzene compounds which are present in the crude tBS stream obtained from the oxydehydrogenation reactor, i.e. isopropenylstyrene and butenylstyrene. Careful conventional distillation of the recovered tBS fraction will remove the higher boiling impurities and also most of the butenylstyrene. However, isopropenylstyrene is very difficult to remove by such conventional distillation and will remain with the tBS at a concentration which is above the maximum limit for many applications. For instance, in some polymerization processes the isopropenylstyrene content that can be tolerated must be no more than about 100 ppm.

It is therefore an object of the present invention to provide a process for the refining of t-butylstyrene to contain only trace quantities of divinylaromatic contaminants.

THE DRAWING

The drawing shows an embodiment of the extractive distillation process of the present invention.

THE INVENTION

In accordance with the present invention there is provided a process for the removal of isopropenylstyrene contaminant from a tBS stream comprising, introducing said tBS stream as feed to an extractive distillation zone; subjecting said feed to extractive distillation with sulfolane as solvent; removing refined tBS overhead and removing sulfolane containing isopropenyl contaminant as bottoms.

In the past sulfolane has been used for the separation of aromatics from non-aromatics such as paraffins. It was unexpectedly found that sulfolane could be used to separate one aromatic from another closely related aromatic. It was also found that the separation could be carried out without any significant problems with unwanted polymerization provided that the separation was carried out under extractive distillation conditions.

The invention will be better understood by reference to the accompanying figure which is a schematic drawing of the apparatus in which the instant process is performed.

In a typical operation the tBS feed, containing small quantities of contaminants including isopropenylstyrene and butenylstyrene is fed in line 1 to an intermediate point of a trayed extractive distillation column 2, and sulfolane, usually with added inhibitor, is fed through line 3 to a higher region of the column. The overhead vapors 4 are condensed in reflux condenser 5, the portion 6 of the condensate being returned as column reflux, while the remaining portion 7 is removed as distillate product. A portion 9 of the bottoms 8 is passed through reboiler 10 and returned to the column to provide heat thereto, and the remaining bottoms are removed in line 11.

The weight ratio of sulfolane to t-butylstyrene feed should range between about 1:1 to about 10:1.

The polymerization inhibitor can be any one effective in supressing polymerization of tBS and aromatic divinyl compounds. Suitable inhibitors include 2,4-dinitrophenol and 2,6-dinitro-m-cresol. The inhibitor should be added near the top of the column such that it is present within the entire liquid phase in the column. The concentration of inhibitor in the liquid in the column should range between about 100 and about 10,000 ppm by weight, preferably between about 500 and about 5000 ppm.

The external reflux ratio, i.e. the weight ratio of the stream quantities in lines 6 and 7 can be varied considerably and is suitably maintained between about 1:1 and about 10:1.

The extractive distillation column should be operated under reduced pressure. In order to minimize polymerization of tBS it is necessary to operate the column at as low temperatures as possible while at the same time keeping the liquid hold-up as low as possible and still maintaining adequate production rates. The pressure should therefore be maintained in the region between about 10 and about 100 mm Hg and preferably between about 20 and 50 mm Hg. At pressures below 10 mm Hg the capacity of the column would be lower and although the liquid hold-up might be unaffected by the lower pressure, the decrease in throughput would partially offset the gains in the form of longer residence times even though it would be at a lower temperature.

In the operation of the extractive distillation column it is possible to obtain an overhead stream of tBS containing very small quantities of isopropenylstyrene, i.e. below 100 ppm. In addition, any other tBS feed contaminants, such as butenylstyrene have also been reduced by the extractive distillation to even lower concentrations.

A small amount of sulfolane is usually present in the overhead in amounts from about 1 to about 5 wt. %. The sulfolane is easily removed by one or more washes in extraction zone 12 with water entering in line 13 and exiting in line 14. The washed tBS can, if desired, be dried (not shown) before it is sent to final product storage.

The bottoms product in line 11 containing the sulfolane solvent and the extracted impurities is usually recycled to the process. To prevent excessive accumulation of the impurities in the sulfolane, it is preferable that at least a portion of said sulfolane be treated e.g. by periodic or continuous distillation, for removal of such impurities.

The following example illustrates the invention.

EXAMPLE 1

A tBS stream containing about 1000 ppm of isopropenylstyrene is refined by extractive distillation in a still having a 15 ft. column made of steam-jacketed section of stainless steel pipe of 3 inches diameter. At the top there is a condenser equipped with a reflux dividing valve. An electrically heated flat bottom reboiler, equipped with a level detector and control valve is provided at the bottom of the column. The tBS feed is vaporized by preheating it to 140° C. and it is fed to the column at a point 10 ft. from the top and at a rate of about 1.5 liters per hour. Sulfolane containing circa 5000 ppm 2,4-dinitrophenol is introduced at 135° C. to the column about 1 ft. below the top of the column at a rate of about 3 liters per hour. The reflux ratio is kept at about 2:1 L/D, the pressure (overhead) at about 50 mm Hg, column top temperature at about 135° C. and the bottom temperature at about 180° C.

An overhead product of refined tBS is collected at a yield of 99 wt. % and containing about 50 ppm of isopropenylstyrene. The distillate also contains butenylstyrene.

It is obvious to those skilled in the art that many variations and modifications may be made without departing from the spirit and scope of the invention as herein described and defined in the appended claims.

What is claimed is:

1. A process for the refining of a t-butylstyrene stream containing isopropenylstyrene comprising:
   introducing said stream as feed to an extractive distillation zone; subjecting said feed to extractive distillation with sulfolane as solvent; removing overhead refined t-butylstyrene depleted in isopropenylstyrene and removing sulfolane-containing isopropenylstyrene as bottoms.

2. The process of claim 1 wherein the weight ratio of sulfolane to t-butylstyrene introduced with the feed to the extractive distillation zone is maintained between about 1:1 and about 10:1.

3. The process of claim 1, wherein a portion of the overhead after condensation is returned to the top portion of the extractive distillation zone to provide a reflux ratio in the range between about 1:1 and about 10:1.

4. The process of claim 1 wherein the pressure of distillation zone is maintained between about 10 and about 100 mm of Hg.

5. The process of claim 4 wherein said pressure is between about 20 and about 50 mm Hg.

6. The process of claim 1 wherein the feed to the extractive distillation zone is vaporized.

7. The process of claim 1 wherein a polymerization inhibitor is introduced to the extractive distillation zone to provide a concentration in the liquid in the zone of from about 100 to about 10,000 ppm by weight.

8. The process of claim 7 wherein said concentration is between about 500 and about 5,000 ppm.

9. The process of claim 7 wherein the polymerization inhibitor is selected from the group consisting of 2,4-dinitrophenol and 2,6-dinitro-m-cresol.

10. The process of claim 7 wherein the polymerization inhibitor is introduced to the extractive distillation zone at the location of the sulfolane feed introduction.

* * * * *